Figure 1:
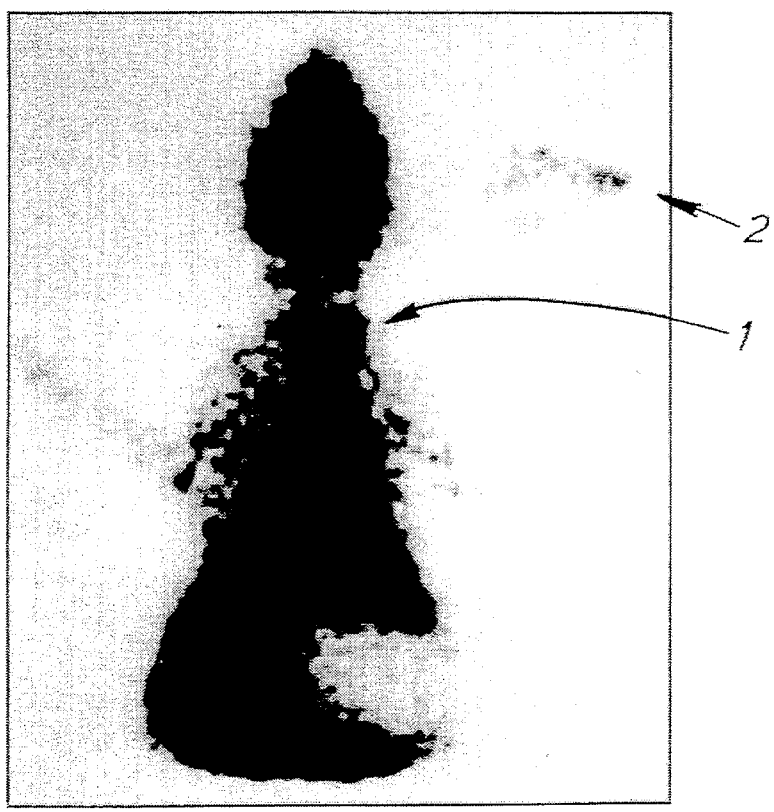

United States Patent [19]

Stuttle

[11] Patent Number: 5,395,609
[45] Date of Patent: Mar. 7, 1995

[54] SYNTHETIC PEPTIDES FOR USE IN TUMOR DETECTION

[75] Inventor: Alan W. J. Stuttle, London, United Kingdom

[73] Assignee: Antisoma Limited, London, Great Britain

[21] Appl. No.: 57,045

[22] Filed: May 3, 1993

Related U.S. Application Data

[63] Continuation-in-part of Ser. No. 659,343, filed as PCT/GB 90/00933, Jun. 18, 1990, published as WO 90/15818, Dec. 27, 1990 abandoned.

[30] Foreign Application Priority Data

Jun. 19, 1989 [GB] United Kingdom ............... 8914020

[51] Int. Cl.⁶ ............................................. A61K 49/02
[52] U.S. Cl. ................................ 424/1.69; 424/1.45
[58] Field of Search ........................... 424/1.45, 1.69; 530/328, 329, 330, 331

[56] References Cited

U.S. PATENT DOCUMENTS

| | | | |
|---|---|---|---|
| 4,427,646 | 1/1984 | Olexa et al. | 424/1.1 |
| 4,614,517 | 9/1986 | Ruoslahti et al. | 530/330 |
| 4,683,291 | 7/1987 | Zimmerman et al. | 530/328 X |
| 4,753,875 | 6/1988 | Ryan | 435/7.4 |
| 4,792,525 | 12/1988 | Ruoslahti et al. | 530/324 X |
| 4,952,562 | 8/1990 | Klein et al. | 530/330 X |
| 4,957,902 | 9/1990 | Grinnell | 530/329 X |
| 4,986,979 | 1/1991 | Morgan, Jr. et al. | 424/1.53 |
| 5,053,392 | 10/1991 | Klein et al. | 530/330 X |
| 5,100,875 | 3/1992 | Marguerie de Rotrou | 530/330 |
| 5,183,804 | 2/1993 | Saiki et al. | 530/327 X |
| 5,196,510 | 3/1993 | Rodwell et al. | 530/324 |
| 5,262,520 | 11/1993 | Plow et al. | 530/327 X |
| 5,279,812 | 1/1994 | Krstenansky et al. | 424/1.69 |
| 5,328,840 | 7/1994 | Coller | 530/300 X |

FOREIGN PATENT DOCUMENTS

| | | |
|---|---|---|
| 0063002 | 3/1982 | European Pat. Off. . |
| 0205270 | 5/1986 | European Pat. Off. . |
| 0333356 | 3/1989 | European Pat. Off. . |

OTHER PUBLICATIONS

Burns et al., *J. Cell Biology,* vol. 107, pp. 1225–1230 (Sep. 1988).

Saiki et al., *Br. J. Cancer,* vol. 60, pp. 722–728 (1989).

D'Souza et al., *J. Biol. Chem.,* vol. 263, No. 8, pp. 3943–3951 (Mar. 1988).

Michael D. Pierschbacker, et al., Cell Attachment Activity of Fibronectin Can Be Duplicated By Small Synthetic Fragments of the Molecule, Nature, vol. 309, pp. 30–33, May 3, 1984.

G. E. Hanks, M.D., et al., The Outcome of Treatment of 313 Patents With T-I (UICC) Prostate Cancer Treated With External Beam Irradiation, Int'l. Radiation Onocology Biol. Phys., vol. 14, No. 2, pp. 243–248, Feb. 1988.

Marek Kloczewiak, et al., Platelet Receptor Recognition Domain On the τ Chain of Human Fibrinogen and Its Synthetic Peptide Analogues, Biochemistry, vol. 28, No. 7, pp. 2915–1919, 1989.

Marek Kloczewiak, et al., Platelet Receptor Recognition Site On Human Fibrinogen. Synthesis and Structure–Function Relationship of Peptides Corresponding To the Carboxy–Terminal Segment of the τ Chain, Biochemistry, vol. 23, pp. 1767–1774, 1984.

Jacek Hawiger, et al., Platelet Receptor Recognition Domains On The α Chain of Human Fibrinogen: Structure–Function Analysis, Biochemistry, vol. 28, pp. 2909–2914, 1989.

*Primary Examiner*—Robert L. Stoll
*Assistant Examiner*—John M. Covert
*Attorney, Agent, or Firm*—Fay, Sharpe, Beall, Fagan, Minnich & McKee

[57] ABSTRACT

Radioactively labelled peptides comprising oligopeptides of from 3 to 10 peptide units and containing the sequence RGD and particularly the oligopeptides RGDSY and RGDFY, are disclosed as in vivo thrombus, tumor or CAM markers for the in vivo diagnosis and detection of thrombi, tumors or CAM in mammals.

4 Claims, 3 Drawing Sheets

SYNTHETIC PEPTIDES FOR USE IN TUMOR DETECTION

This is a continuation-in-part of application Ser. No. 07/659,343, filed as PCT/GB 90/00933, Jun. 18, 1990, published as WO 90/15818, Dec. 27, 1990, now abandoned.

This invention relates to the development and use of synthetic peptides for thrombus detection both in human beings and animals, but primarily, of course, in the detection of human disease. The method and the synthetic peptides used therein are also useful in targetting other sites in vivo, e.g., cell adhesion molecules (CAMs) and tumors, containing an RGD binding site.

In 1984 Pierschbacher and Ruoslahti (Nature, 309, 30–33), showed evidence that the cell attachment activity of fibronectin could be mimicked by small synthetic peptide fragments. The amino acid sequence responsible for this activity was shown to be Arg-Gly-Asp-Ser (RGDS) and it was demonstrated that synthetic peptides containing this sequence were able to inhibit attachment of NRK cells (cells from a neuroblastoma cell line) to fibronectin coated substrates. The inhibition obtained with RGDS containing peptides was shown to be dose-related, while peptides which did not contain the RGDS sequence failed to inhibit cell attachment. The serine residue of the tetrapeptide has been shown to be non-essential, although only conservative substitutions may be made in order to retain biological activity.

The RGDS sequence has been shown to occur in fibrinogen, fibronectin and von Willebrand factor. Receptors for these proteins are expressed on the platelet membrane surface following platelet activation. Cross-linking of platelets via these cytoadhesive proteins accounts for the platelet-platelet interactions within a thrombus. It has also been demonstrated that RGDS containing synthetic peptides are capable of inhibiting platelet aggregation in vitro. This would suggest a specific interaction with the GP IIb/IIIa (glycoprotein fibrinogen receptor) complex present on the platelet membrane surface, which contains the fibrinogen binding domains. Extension of the RGDS sequence, by one amino acid residue at the carboxy and amino terminal, results in a ten-fold reduction in its biological activity, although further extension is not associated with a further reduction in binding capacity. Substitution of the serine residue by phenylalanine results in an anti-aggregatory peptide which is 4 to 5 times more potent than RGDS. There has also been suggestion that the residue corresponding to serine in the RGDS sequence may impart a degree of recognition specificity for different RGDS receptors. This raises the possibility that both specificity and affinity could be modified by substitution around the RGD sequence. RGD binding sites are also known to occur on cell adhesion molecules (CAMs) and some tumors.

The present invention involves a novel approach to in vivo thrombus and/or tumor detection and which comprises the intravenous injection into the patient (which term herein includes both humans and animals, unless the context requires otherwise) of a radioactively labelled synthetic peptide having therein an RGD (Arg-Gly-Asp)-containing sequence, preferably an RGDS (Arg-Gly-Asp-Ser) or RGDF (Arg-Gly-Asp-Phe)-containing sequence having a specific binding affinity for RGD binding sites such as for the platelet GP IIb/IIIa complex, and detecting the presence, if present, of the bound label on the thrombus and/or tumor. Present methods of thrombus and/or tumor detection using labelled antibodies require several hours due to the slow rate of diffusion of the antibody through the system; using labelled peptides in accordance with the present invention is expected to enable thrombus and/or tumor detection in a matter of minutes, thus greatly facilitating diagnosis and treatment, and at a very early stage.

For use in that method of in vivo thrombus and/or tumor detection there is provided in accordance with the present invention a synthetic peptide containing the sequence RGD, preferably as RGDS or RGDF, and labelled with a radioactive label.

Suitable radioactive labels for use in the construction of such radioactively labelled peptides include: $Tc^{99m}$, $I^{123}$ and $In^{111}$, and will be attached to the synthetic peptide in known manner, for example, via a cystine residue in the synthetic peptide. Other suitable techniques are described in Science, 220, 613–615; Int. J. Nucl. Med. Biol., 12, 3–8; J. Nucl. Med., 27, 27, 685–693 and J. Nucl. Med., 26, 293–299.

Subject to the dictates of suitability for parenteral administration and utility, i.e. high affinity and specificity for the GP IIb/IIIa complex, the precise amino acid sequence in terms of composition and length will not be particularly critical, although for practical reasons, e.g. economy and ease of synthesis, relatively short chain peptides will be preferred containing, for example, from 3 to 10 peptide units.

Suitable peptides containing an RGD sequence, preferably an RGDS or RGDF are available frown a variety of different sources, or can be manufactured quite readily using conventional peptide synthesis procedures, and, in particular, using a conventional peptide synthesiser.

Also included within the scope of this invention are a diagnostic reagent for in vivo thrombus and/or tumor detection comprising a parenterally administrable solution of the radioactively labelled peptide containing an RGD sequence and a parenterally administrable carrier, and a method of in vivo thrombus and/or tumor detection which comprises intravenously administering a radioactively labelled peptide containing and RGD sequence capable of binding to RGD binding sites on platelets in the thrombus and/or tumor and radiographically detecting the accumulated bound peptide.

The invention also extends to the use of the radioactively labelled peptides in in vivo localisation on to the RGD binding sites of CAMs.

Before proceeding further with the detailed description of this invention, and for the avoidance of doubt, the amino acid sequences referred to herein are identified by either their three letter abbreviations or single letter codes, as follows:

| | | |
|---|---|---|
| arginine | = | arg. or R. |
| aspartic acid | = | asp. or D. |
| glycine | = | gly. or G. |
| serine | = | ser. or S |
| tyrosine | = | tyr. or Y |
| phenylalanine | = | phe. or F |
| cysteine | = | cys. or C |

Figure 2:
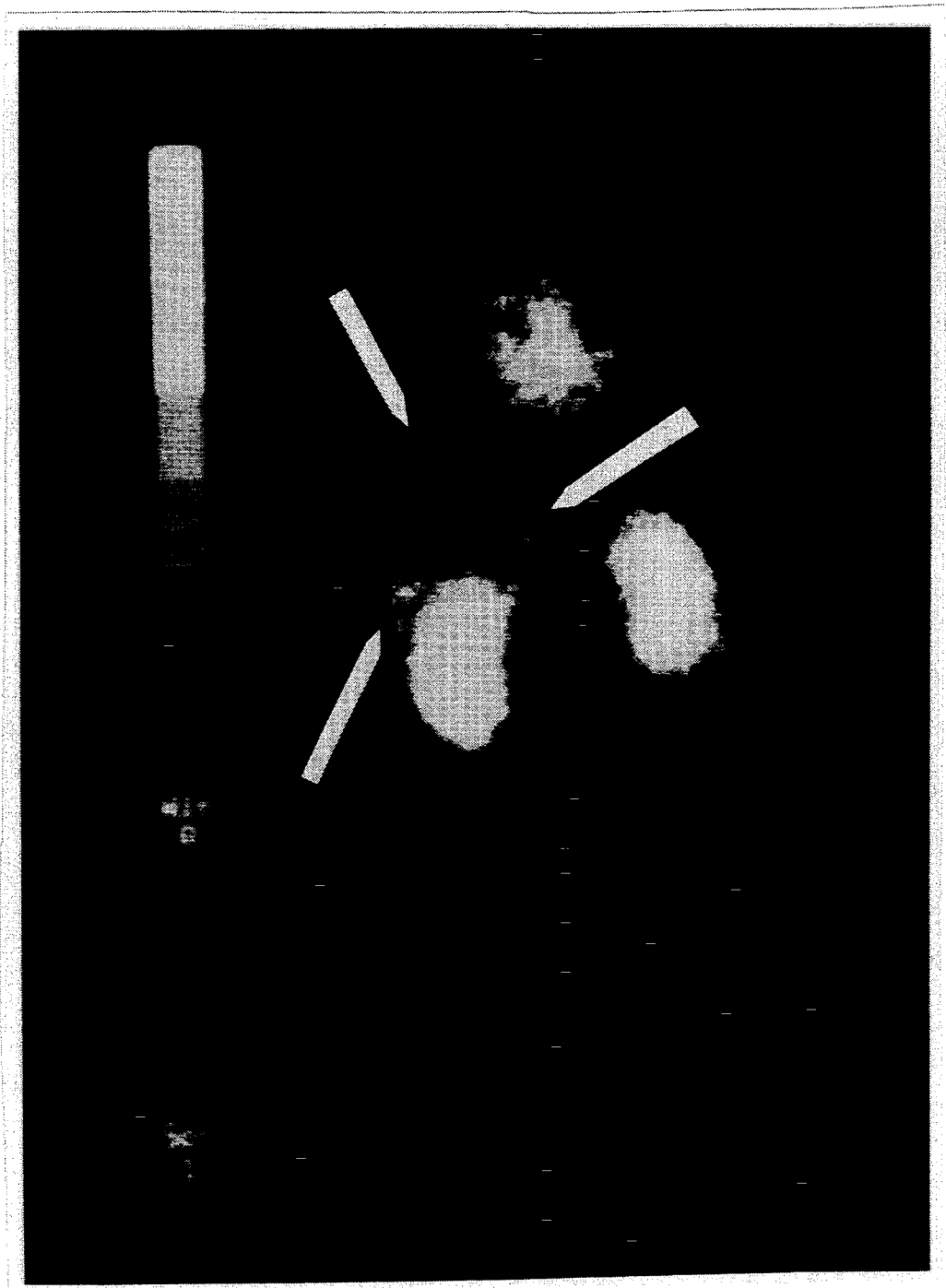
Figure 3:
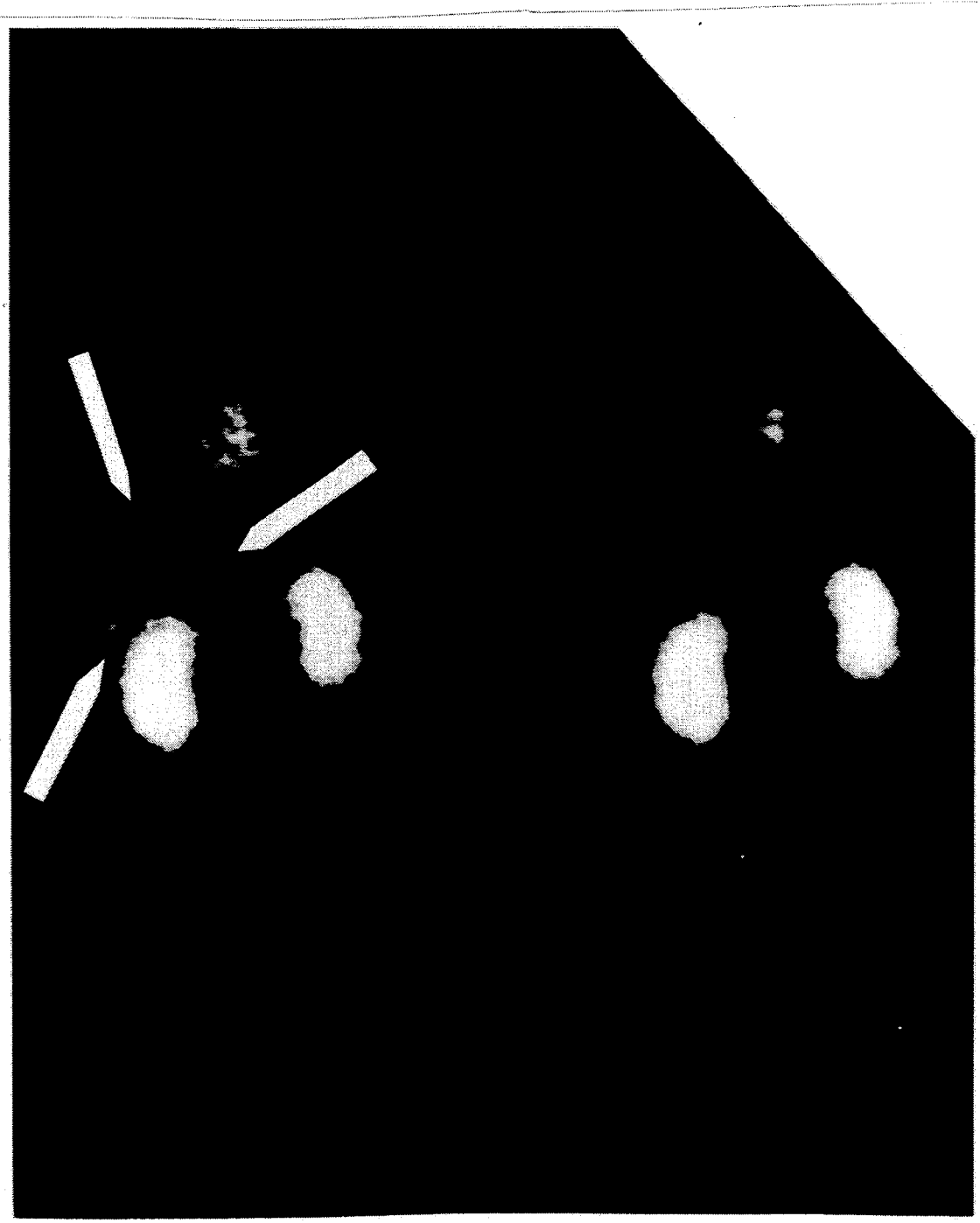

Reference is also made hereinafter to the accompanying figures, wherein FIG. 1 is a radiograph taken of a rabbit following intravenous administration of a radioactively labelled peptide according to this invention, and showing the localisation of the peptide in an artificially induced thrombus in the left ear. FIGS. 2 and 3 are photographic scans obtained from a human patient with pelvic melanoma which has metastasized to the liver. FIG. 2 shows an early view of the patient demonstrating various stages of uptake (arrow) which corresponds to the known metastatic lesions. FIG. 3 shows the same patient one hour later demonstrating the retention of the radiolabelled peptide by the metastatic lesions.

Referring to the invention in slightly more detail, studies have been conducted using four peptides (RGDSY, RGDFY, RGDSYC and RGDSCRGDSY) to evaluate their potential as thrombus and/or tumor imaging agents.

The effect of these peptides on ADP-induced platelet aggregation was determined and compared with peptide RGDS which is known to inhibit platelet aggregation. The results (table 1) demonstrate that all four peptides studied are capable of inhibiting platelet aggregation at high concentrations and are virtually equipotent with RGDS. This suggests that inclusion of amino acids into these peptide sequences, to permit radio-labelling, does not destroy their ability to bind platelets (a prerequisite for thrombus imaging applications).

The second study involved radiodination of RGDSY, RGDFY, RGDSYC and RGDSCRGDSY with subsequent analysis of their ability to bind activated platelets in whole blood. The results (Table 2) indicate that all four peptides can bind platelets in ADP stimulated blood and that higher incorporation can be achieved in clotted blood.

One study was performed using RGDSY, labelled with the radioisotope iodine-123, injected into a rabbit who had a preformed thrombus in the microvasculature of the ear. The imaging studies, shown in the accompanying figure demonstrates a rapid uptake onto this thrombus (within 2 minutes of injection), which persisted for the period of study (20 minutes).

These data demonstrate that the four peptides studied are capable of binding to platelets, can be radiolabelled with gamma-emitting isotopes and are incorporated into platelet aggregates in stimulated and clotted blood. This provides good potential for thrombus detection and diagnosis by these peptides in vivo which has been confirmed, in an experimental animal model, using one of the peptides.

TABLE 1

Inhibition of ADP ($1 \times 10^{-5}$ M) -induced platelet aggregation by RGDS, RGDSY, RGDFY, RGDSYC and RGDSCRGDSY peptides.

| | (peptide) percentage inhibition | | | | |
|---|---|---|---|---|---|
| mM | RGDS | RGDSY | RGDFY | RGDSYC | RGDSC-RGDSY |
| 0.1 | 40/37 | 5/13 | 32 | 25 | 17 |
| 0.2 | 70/65 | 10/21 | 55 | — | 57 |
| 0.4 | 86/80 | 43/68 | 80 | — | 79 |

TABLE 2

Binding of radiolabelled RGDSY, RGDFY, RGDSYC and RGDSCRGDSY peptides to ADP stimulated and clotted blood.

| | (peptide) (bound peptide) ng | | | |
|---|---|---|---|---|
| ng | RGDSY | RGDFY | RGDSYC | RGDSCRGDSY |
| ADP Stimulated blood | | | | |
| 1 | 0.05 | 0.01 | 0.03 | 0.01 |
| 10 | 0.64 | 1.00 | 0.94 | 0.85 |
| 100 | 9.80 | 4.46 | 9.85 | 9.07 |

TABLE 2-continued

Binding of radiolabelled RGDSY, RGDFY, RGDSYC and RGDSCRGDSY peptides to ADP stimulated and clotted blood.

| | (peptide) (bound peptide) ng | | | |
|---|---|---|---|---|
| ng | RGDSY | RGDFY | RGDSYC | RGDSCRGDSY |
| Clotted Blood | | | | |
| 1 | 0.27 | 0.41 | 0.18 | 0.28 |
| 10 | 0.85 | 2.14 | 2.26 | 2.64 |
| 100 | 17.27 | 18.12 | 27.08 | 29.33 |

The above results demonstrate the applicability of the invention over a range of synthetic peptides of different sizes all containing an RGD sequence. The actual length of the peptides is not critical, but for practical purposes the chain lengths may range from 3 to 10 peptide units, preferably 4 to 10 and, as already indicated, either consisting of or comprising an RGDS or RGDF sequence. Many such synthetic peptides are already available as known commercial products. Where not so available they can be readily synthesised by known peptide syntheses and/or using known peptide synthesisers. Similarly said synthetic peptides can be radioactively labelled by known techniques, for example, by iodination with $I^{123}$ of a terminal tyrosine (Y) unit incorporated into the peptide.

A third study involved the use of 100 micrograms of a peptide containing the sequence RGD, and particularly RGDSCRGDSY, labelled with technetium administered intravenously and retention of the radiolabelled peptide by the metastatic lesions.

The detailed preparation and use of radioactively labelled peptides according to this invention is illustrated by the following examples.

EXAMPLE 1

Preparation of Radioactively Labelled ($I^{123}$) RGDSY, RGDFY, RGDSYC and RGDSCRDSY Iodogen tubes were prepared by dissolving Iodogen (1, 3, 4, 6-Tetrachloro-3α, 6α-diphenylglycouril) in chloroform at a concentration of 1 mg.ml$^{-1}$. Aliquots of 50 μl (50 μg Iodogen) were dispensed into polypropylene cryo-tubes and the chloroform evaporated to dryness. These tubes were then stored dessicated at −20° C. until required.

Prior to radiolabelling the peptides were dissolved in phosphate buffered saline (PBS) at a concentration of 50 μg.ml$^{-1}$. RGDSYC and RGDSCRGDSY were first dissolved in a small volume of dimethyl sulphoxide (DMSO) such that the final concentration of DMSO in PBS was 1% v/v.

Iodogen tubes were equilibrated to room temperature before the addition of 200 μl peptide solution and 1–10 μl of $^{123}$I (in aqueous solution). The reaction mixture was then left for 15 min at room temperature with occasional shaking. Following the incubation period the reaction mixture was removed and passed through a Sephadex G10 column which had been equilibrated with PBS. The column, which separates radiolabelled peptide from free iodine was eluted with PBS and 2 ml fractions collected. Radioactivity in the fractions was measured and the eluted peptides, represented by the first radioactive peak from the column, collected and stored at 4° C. until required.

The utility of the radioactively labelled peptides in in vivo thrombus detection is illustrated by the following experiment.

EXPERIMENT

Intravenous Administsration of Radioactively Labelled ($I^{123}$) RGDSY to Thrombitic Rabbits A male New Zealand White rabbit (3 kg) was sedated by intramuscular injection of Hypnorm (0.4 ml.kg$^{-1}$) and then anaesthetised by intravenous injection of Midazolam (2 mg.kg$^{-1}$).

Two permanent disc magnets were positioned externally in the region of the jugular vein and the rabbit was then injected with 0.2 g carbonyl iron microspheres suspended in 1 ml of contrast media (Omnipaque) via an artery of the left ear. This procedure causes microthrombi in the capillary beds of the ear, whilst iron particles passing through the ear are trapped by the magnetic field and induce thrombus formation in the jugular vein. $^{123}$I-RGDSY was injected intravenously into the contralateral ear 60 min after injection of iron. Dynamic imaging by gamma camera was performed using a 1 min frame rate for 20 min with the camera positioned anteriorly to include both ears, head and neck regions in the field of view.

Following intravenous administration of the labelled peptide, the rabbit was radiographed and the resulting radiograph is presented in the accompanying figure. As indicated by the radiograph, there was rapid uptake of the peptide by a thrombus in the jugular vein (arrow 1) and by multiple tiny thrombi in the left ear (arrow 2). The latter, in particular, demonstrates the possible utility of the invention in the detection of small thrombi in vivo and the possibility of early diagnosis and treatment.

EXAMPLE 2

100 micrograms of the peptide RGDSCRGDSY labelled with technetium were administered intravenously as one single dose to a human patient with a pelvic melanoma which has metastrasised to the liver. FIG. 2 is a photographic scan which shows an early view in this patient demonstrating various sites of uptake (arrow) which correspond to the known metastatic lesions. FIG. 3 is a photographic scan which shows the same patient viewed one hour later and demonstrating the retention of the radiolabelled peptide by the metastatic lesions.

I claim:

1. A method for the in vivo imaging of a tumor having on its surface RGD binding sites comprising the steps of intravenously administering radioactively labelled peptides containing from 3-10 peptide units and having an RGD sequence capable of binding to RGD binding sites on the tumor, allowing for the labelled peptides to bind to the RGD binding sites and for the unbound labelled peptides to systemically clear from the patient, and radiographically detecting the accumulated bound peptides.

2. The method according to claim 1, wherein the peptides are at least one peptide selected from the group of peptides consisting of RGDSY, RGDFY, RGDSYC and RGDSYCRGDSY to which a radioactive label has been attached.

3. A method for the in vivo imaging of a tumor having on its surface RGD binding sites comprising the steps of:

a) intravenously administering about 100 micrograms of labelled peptides, wherein said peptides contain from 3 to 10 peptide units and wherein 3 of the peptide units are the sequence arginine-glycine-aspartic acid, said sequence having the ability to bind to RGD binding sites on platelets forming the thrombus;

b) allowing a sufficient period of time for the labelled peptides to bind to the RGD binding sites and for the unbound labelled peptides to systemically clear from the patient and, c) detecting the accumulated bound peptides.

4. The method of claim 3, wherein the labelled peptides are selected from the group of peptides consisting of RGDSY, RGDFY, RGDSYC and RGDSCRGDSY to which a radioactive label has been attached.

* * * * *